United States Patent [19]

Gerke et al.

[11] Patent Number: 5,247,100
[45] Date of Patent: Sep. 21, 1993

[54] PROCESS FOR THE PRODUCTION OF SCLAREOLIDE

[75] Inventors: Thomas Gerke, Neuss; Klaus Bruns, Krefeld-Traar, both of Fed. Rep. of Germany

[73] Assignee: Henkel Kommanditgesellschaft auf Aktien, Duesseldorf, Fed. Rep. of Germany

[21] Appl. No.: 862,560

[22] PCT Filed: Dec. 13, 1990

[86] PCT No.: PCT/EP90/02166
§ 371 Date: Jun. 22, 1992
§ 102(e) Date: Jun. 22, 1992

[87] PCT Pub. No.: WO91/09852
PCT Pub. Date: Jul. 11, 1991

[30] Foreign Application Priority Data

Dec. 21, 1989 [DE] Fed. Rep. of Germany ....... 3942358

[51] Int. Cl.$^5$ .............................................. C07D 307/92
[52] U.S. Cl. .................................... 549/299; 560/256; 549/389
[58] Field of Search .......................... 549/299; 562/256

[56] References Cited

U.S. PATENT DOCUMENTS 3,050,532  8/1962  Schumacher et al. ............. 549/299
3,096,346  7/1963  Giles et al. ......................... 549/299

OTHER PUBLICATIONS

Cambie et al., Aust. J. Chem., 43(7), 1151–62 (1990).

Primary Examiner—Marianne M. Cintins
Assistant Examiner—John Peabody
Attorney, Agent, or Firm—Ernest G. Szoke; Wayne C. Jaeschke; Henry E. Millson, Jr.

[57] ABSTRACT

A process for the production of sclareolide from sclareol comprising the steps of
A) oxidatively degrading sclareol to a reaction product which is one or both of the following compounds:

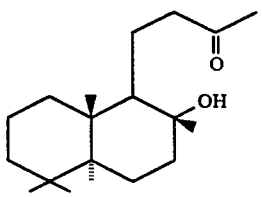

I

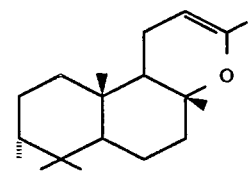

II using either a hypochlorite salt in the presence of a ruthenium salt or potassium permanganate, and
B) oxidizing the above reaction product with a peracid or salt thereof to form sclareolide.

The above process results in good yields and much shorter reaction times than prior art processes.

20 Claims, No Drawings

PROCESS FOR THE PRODUCTION OF SCLAREOLIDE

This invention relates to a process for the production of sclareolide from sclareol.

8α, 12-oxido-13,14,15,16-tetranorlabdane (Ambroxan®) is an extremely valuable amber fragrance which is found in ambergris, a metabolism secretion of the sperm whale (Ullmann's Encyklopädie der Technischen Chemie, Vol. 20, page 283, Verlag Chemie Weinheim, 1981). Synthetically, Ambroxan® can be prepared from sclareol by two-stage oxidation in accordance with U.S. Pat. No. 3,050,532 and subsequent reduction of the sclareolide formed. During the two-stage oxidation process, sclareol (1) is first oxidized with potassium permanganate under alkaline reaction conditions to form the hydroxyketone (2). The hydroxyketone formed is converted without isolation into the enolether (3) by reaction with glacial acetic acid and is subsequently oxidized either with potassium manganate or with chromic acid. The oxidation product obtained, a mixture of sclareolide and acetoxy acid, is saponified and completely cyclized to sclareolide (4). However, the disadvantage of this process lies in the long reaction time of the second oxidation stage. According to the Examples of U.S. Pat. No. 3,050,532, it is about 19.5 hours.

Accordingly, the problem addressed by the present invention was to provide a process for the production of sclareolide which would not require long reaction times. The reduction in the reaction time would be accompanied by at least as good yields of sclareolide as can be obtained with the process known from U.S. Pat. No. 3,050,532.

It has surprisingly been found that the reaction times can be considerably reduced if, in a first stage, sclareol is oxidatively degraded either with hypochlorite salts in the presence of ruthenium compounds or, as in U.S. Pat. No. 3,050,532, with potassium permanganate and, in a second stage, the hydroxyketone obtained is oxidized with peracids and/or salts thereof to sclareolide.

Accordingly, the present invention relates to a two-stage process for the production of sclareolide from sclareol, characterized in that, in a first stage, sclareol is oxidatively degraded to the hydroxyketone 2 and/or the enolether 3 either with hypochlorite salts in the presence of ruthenium compounds or in known manner with potassium permanganate and, in a second stage, the hydroxyketone 2 and/or the enolether 3 is oxidized to sclareolide with peracids and/or peracid salts.

In the process according to the invention, sclareol can be oxidatively degraded to the hydroxyketone 2 and/or the enolether 3 with alkali metal and/or alkaline earth metal hypochlorites, for example sodium and/or calcium hypochlorite, in the presence of ruthenium

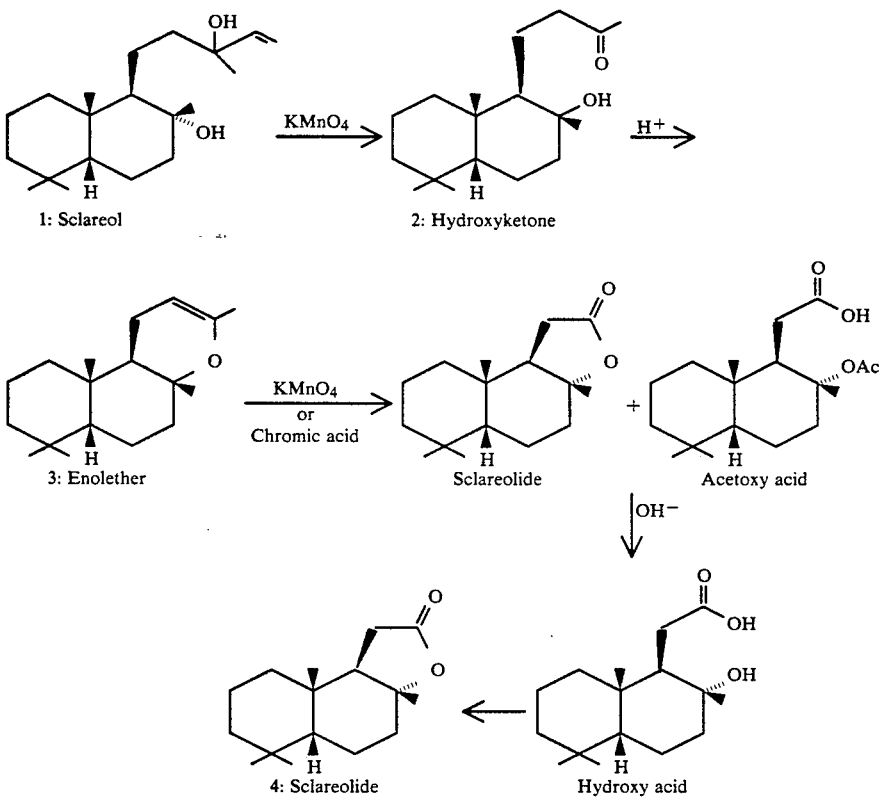

In addition, it is known from DE 36 10 063 that sclareol can be oxidized with hydrogen peroxide in the presence of acids, for example p-toluenesulfonic acid, to form a hydroperoxide from which Ambroxan® can be prepared with a redox system, for example FeSO$_4$/Cu(OAc)$_2$. In this process, too, a long reaction time, namely 7 days, is required for the oxidation stage.

salts, for example ruthenium dioxide and/or ruthenium trichloride, at temperatures of 0° to 40° C. It can be useful to carry out the reaction in the presence of phase transfer catalysts, for example ammonium compounds, such as tetrabutyl ammonium chloride. Sclareol is dissolved in solvents inert under the reaction conditions, for example methylene chloride and/or cyclohexane, preferably with 0.1 to 10 mol-% and, more preferably, with 0.5 to 3 mol-% ruthenium compounds and preferably with 0 to 20 mol-% and, more preferably, with 0 to 10 mol-% phase transfer catalysts (all mol-% are based on sclareol). To these solutions are added aqueous solutions preferably containing 400 to 1,000 mol-% and, more preferably, 600 to 800 mol-% hypochlorite salts and preferably 0 to 500 mol-% and, more preferably, 100 to 500 mol-% alkali metal hydroxides, such as sodium and/or potassium hydroxide, based on the quantity of sclareol used. On completion of the reaction, acids, for example formic acid, acetic acid, hydrochloric acid and/or sulfuric acid, may be added to the reaction mixture so that the corresponding enolether is formed from the hydroxyketone formed. The organic phase is then separated from the aqueous phase and worked up by methods known per se and the solvents are removed by distillation.

Another method of oxidatively degrading sclareol is to add potassium permanganate to sclareol in accordance with U.S. Pat. No. 3,050,532. In this case, sclareol is reacted in the form of an aqueous solution with, based on the quantity of sclareol used, preferably 300 to 600 mol-% and, more preferably, 350 to 550 mol-% potassium permanganate, the reaction being carried out with vigorous stirring at temperatures in the range from 20° to 40° C. In order to remove manganese dioxide on completion of the reaction, the reaction mixture is either adjusted with acids, for example sulfuric acid, to a pH value of 2 and $SO_2$ subsequently introduced at 5° to 10° C until the manganese dioxide has completely dissolved or is extracted with organic solvents, such as diethyl ether, methylene chloride or toluene.

The hydroxyketone 2 and/or the enolether 3 obtained by one of the two methods described above (before the oxidation stage, the hydroxyketone may optionally be converted into the enolether 3 with acids, such as formic acid, acetic acid, hydrochloric acid and/or sulfuric acid) is/are oxidized to sclareolide with peracids and/or salts thereof at temperatures of 10° to 60° C. Examples of suitable peracids and/or peracid salts are performic acid, which is preferably formed in situ from formic acid and hydrogen peroxide, peracetic acid, monoperoxyphthalic acid, magnesium monoperoxyphthalate and/or m-chloroperbenzoic acid. The peracids and/or peracid salts are preferably used in quantities of 100 to 500 mol-% and, more preferably, in quantities of 100 to 300 mol-%, based on the quantity of hydroxyketone and/or enolether used. On completion of oxidation, the oxidation product is saponified with alkalis, for example sodium hydroxide and/or methanolic KOH, and the non-saponifiable constituents are removed by methods known per se. After acidification, the hydroxy acid formed is filtered off and is then cyclized to sclareolide at temperatures of 130° to 160° C.

Reaction times considerably shorter than those of known processes are sufficient for the production of sclareolide from sclareol by the process according to the invention. For example, the second oxidation stage of the process according to the invention lasts about 3 hours whereas the reaction time of the second oxidation stage of the process known from U.S. Pat. No. 3,050,532 (for substantially the same quantities of sclareol used) is about 19 to 20 hours. At 65 to 70%, based on sclareol, the yield of sclareolide is at least as high as in the processes known from the prior art.

EXAMPLES

Oxidative degration of sclareol 123.2 g sclareol were dissolved in 500 ml methylene chloride with 11.8 g tetrabutyl ammonium chloride and 1.2 g $RuO_2$. A solution of 72 g sodium hydroxide in 1530 g sodium hypochlorite (12.6% by weight) was added dropwise to this mixture over a period of 3 hours. The temperature was kept below 25° C. by cooling.

For working up, 37% by weight hydrochloric acid was added to the reaction mixture. The aqueous phase was extracted twice with methylene chloride, the combined organic phases were dried with sodium sulfate and the solvent was removed by distillation in vacuo, leaving 93.4 g of a mixture containing 89.3% enolether (as determined by gas chromatography), which corresponds to a yield of 80%.

Oxidation of the enolether to scalareolide 93.4 g enolether (89.3% pure, as determined by gas chromatography) were added to 1000 ml formic acid. 115 g hydrogen peroxide (30% by weight) were then added dropwise, the temperature being kept below 40° C. by cooling. After stirring for 3 hours, the reaction mixture was extracted with diethyl ether, dried with sodium sulfate and the ether subsequently removed by distillation. The residue obtained was refluxed for 3 hours in a solution of 66 g potassium hydroxide in 90 ml water and 900 ml methanol. Methanol was then distilled off, the residue was dissolved in 2 liters water, the solution was extracted with 2.5 liters hexane and the aqueous phase was adjusted to a pH value of 2 with 20% by weight sulfuric acid. The hydroxy acid precipitated was filtered off and, after drying, was heated to 145° C., cyclizing to sclareolide with elimination of water.

After recrystallization from hexane, sclareolide was obtained in a yield of 65%, based on sclareol.

We claim:

1. A process for the production of sclareolide from sclareol comprising the steps of
    A) oxidatively degrading sclareol to a reaction product which is one or both of the following compounds:

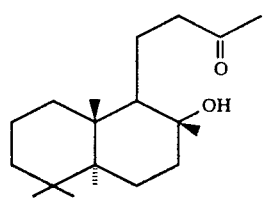

I

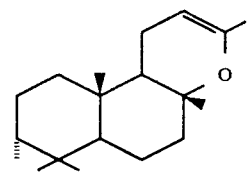

II using either a hypochlorite salt in the presence of a ruthenium salt or potassium permanganate, and
    B) oxidizing the above reaction product with a peracid or salt thereof to form sclareolide.

2. The process of claim 1 wherein in step A sclareol is oxidatively degraded with from about 400 to about 1000 mol % of an alkali metal and/or alkaline earth metal hypochlorite salt in the presence of from about 0.1 to about 10 mol % of a ruthenium salt, the above mol percentages being based on sclareol.

3. The process of claim 2 wherein from about 600 to about 800 mol % of hypochlorite salt and from about 0.5 to about 3 mol % of ruthenium salt is employed in step A.

4. The process of claim 1 wherein in step A sclareol is oxidatively degraded with from about 300 to about 600 mol % of potassium permanganate, the above mol percentages being based on sclareol.

5. The process of claim 4 wherein in step A from about 350 to about 550 mol % potassium permanganate is employed.

6. The process of claim 1 wherein step A is carried out with a hypochlorite salt in the presence of a phase transfer catalyst.

7. The process of claim 1 wherein in step B from about 100 to about 500 mol % period or salt thereof is employed therein, based on the compounds produced in step A.

8. The process of claim 7 wherein in step B from about 100 to about 300 mol % peracid or salt thereof is employed therein based on the compounds produced in step A.

9. The process of claim 7 wherein the peracid or salt thereof is one or more peracids selected from the group consisting of performic acid, peracetic acid, monoperoxyphthalic acid, m-chloroperbenzoic acid, magnesium monoperoxophthalate, and salts of the forgoing.

10. The process of claim 2 wherein step A is carried out at a temperature in the range of from about 0° to about 40° C.

11. The process of claim 2 wherein from about 100 to about 500 mol %, based on sclareol, of alkali metal hydroxide is also present as step A.

12. The process of claim 4 wherein step A is carried out at a temperature in the range of from about 20° to about 40° C.

13. The process of claim 4 wherein the reaction product from step A is treated with an acid to convert the compound of formula I to the compound of formula II prior to carrying out step B.

14. The process of claim 4 wherein the reaction product from step A is treated with an acid to convert the compound of formula I to the compound of formula II prior to carrying out step B.

15. The process of claim 2 wherein step B is carried out at a temperature in the range of from about 10° to about 60° C.

16. The process of claim 1 wherein in step B, after completion of oxidation, the oxidation product is saponified with an alkali, the saponified product is acidified, and the acidified product is cyclized to sclareolide.

17. The process of claim 16 wherein the acidified product is cyclized at a temperature in the range of from about 130° to about 160° C.

18. A process for the production of sclareolide from sclareol comprising the steps of
A) oxidatively degrading sclareol to a reaction product which is one or both of the following compounds:

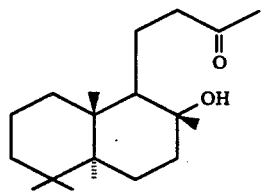

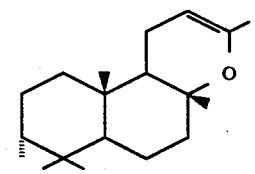

using either a hypochlorite salt in the presence of a ruthenium salt or potassium permanganate,
B) oxidizing the above reaction product with a peracid or salt thereof,
C) saponifying the oxidation product from step B with an alkali,
D) acidifying the saponified product from step C, and
E) cyclizing the acidified product from step D to scalareolide.

19. The process of claim 18 wherein in step A sclareol is oxidatively degraded with either (i) from about 500 to about 1000 mol % of an alkali metal and/or alkaline earth metal hypochlorite salt in the presence of from about 0.1 to about 10 mol % of a ruthenium salt, or (ii) from about 300 to about 600 mol % of potassium permanganate, the above mol percentages being based on sclareol; in step B from about 100 to about 500 mol % peracid or salt thereof is employed therein, based on the compounds produced in step A; and wherein step E is carried out at a temperature in the range of from about 130° to about 160° C.

20. The process of claim 19 wherein in step A either (i) from about 600 to about 800 mol % of hypochlorite salt and from about 0.5 to about 3 mol % of ruthenium salt is present at a temperature of from about 0° to about 40° C., or (ii) from about 350 to about 550 mol % potassium permanganate and from about 100 to about 500 mol % of an alkali metal hydroxide is present at a temperature in the range of from about 0° to about 40° C., and the reaction product from step A is treated with an acid to convert the compound of formula I to the compound of formula II prior to carrying out step B; and in step B from about 100 to about 300 mol % peracid or salt thereof is employed therein based on the compounds produced in step A, and step B is carried out at a temperature in the range of from about 10° to about 60° C.

* * * * *